(12) United States Patent
Wu et al.

(10) Patent No.: US 7,674,733 B2
(45) Date of Patent: Mar. 9, 2010

(54) BREATHABLE AND ELASTIC COMPOSITE MATERIALS AND METHODS

(75) Inventors: Pai-Chuan Wu, Cincinnati, OH (US);
Dale Eugene Robinson, Hamilton, OH (US); Richard Arnold Bradford, Brooksville, KY (US)

(73) Assignee: Clopay Plastic Products Company, Inc., Mason, OH (US)

( * ) Notice: Subject to any disclaimer, the term of this patent is extended or adjusted under 35 U.S.C. 154(b) by 472 days.

(21) Appl. No.: 10/104,725

(22) Filed: Mar. 22, 2002

(65) Prior Publication Data
US 2003/0181120 A1 Sep. 25, 2003

(51) Int. Cl.
*B32B 3/10* (2006.01)
*B32B 37/00* (2006.01)
*B32B 37/15* (2006.01)
*D04H 1/00* (2006.01)
*D04H 3/00* (2006.01)

(52) U.S. Cl. .................. 442/394; 442/382; 442/398; 442/399; 442/401; 428/131; 156/229

(58) Field of Classification Search ............. 442/328, 442/381, 399, 392; 156/229, 244.24, 244.27, 156/324
See application file for complete search history.

(56) References Cited

U.S. PATENT DOCUMENTS

| 5,422,172 | A | 6/1995 | Wu |
| 5,861,074 | A | 1/1999 | Wu |
| 5,865,823 | A | 2/1999 | Curro |
| 5,865,926 | A | 2/1999 | Wu et al. |
| 6,255,236 | B1 | 7/2001 | Cree et al. |
| 6,265,045 | B1 | 7/2001 | Mushaben et al. |
| 6,794,024 | B1 * | 9/2004 | Walton et al. ............. 428/317.9 |
| 2001/0042938 | A1 * | 11/2001 | Mackay ....................... 264/154 |

FOREIGN PATENT DOCUMENTS

| HU | P 9903697 | 2/2000 |
| HU | P 0103996 | 2/2002 |
| HU | P 0103161 | 10/2004 |
| WO | WO 0023273 | 4/2000 |
| WO | WO 0160605 | 8/2001 |

OTHER PUBLICATIONS

"Micro-", Hawley's Condensed Chemical Dictionary, 14th Edition, 2002.*

* cited by examiner

*Primary Examiner*—Jennifer A Chriss
(74) *Attorney, Agent, or Firm*—Dinsmore & Shohl LLP (57) ABSTRACT

In one embodiment, a breathable, incrementally stretched elastic composite material comprises an inner elastomeric film extrusion-laminated to an outer nonwoven web at each film surface. The inner elastomeric film has a random pattern of incremental stretch-formed macroholes therein and is substantially free of pore-forming filler. In another embodiment, a breathable, incrementally stretched elastic composite material comprises an elastomeric film extrusion-laminated to a nonwoven web at one or both of the film surfaces. The elastomeric film has a random pattern of incremental stretch-formed macroholes therein and is substantially free of pore-forming filler. Methods of manufacturing the composite materials comprise extrusion laminating and incremental stretching. Garments and disposable articles are formed at least in part from the composite material.

61 Claims, 4 Drawing Sheets

BREATHABLE AND ELASTIC COMPOSITE MATERIALS AND METHODS

FIELD OF THE INVENTION

The present invention is directed to breathable, incrementally stretched elastic composite materials which comprise an inner elastomeric film extrusion-laminated to a nonwoven web, preferably at each film surface. The invention is further directed to garments and/or disposable articles formed at least in part from such composite materials and to methods of manufacturing such composite materials.

BACKGROUND OF THE INVENTION

Elastic composite materials are known in the art. For example, the Wu U.S. Pat. Nos. 5,422,172 and 5,861,074 disclose elastic laminated sheets of a nonwoven fibrous web and an elastomeric film. Wu defines the term "elastic" as meaning stretchable under force and recoverable to its original or essentially original form upon release of that force. Wu discloses that the elastic laminate may be incrementally stretched to provide a very soft fibrous finish having the appearance of nonwoven fibers with superior bond strengths, thereby providing a composite material advantageous for use in garments and other applications where a soft finish is desirable. Wu further discloses that the elastic laminate is characterized as being impervious to the passage of fluid by virtue of the elastomeric film, while maintaining a soft feel on the fibrous web surface of the laminate, although various degrees of vapor or air permeability may be achieved by providing mechanical microvoids.

Conventional processes for providing mechanical microvoids include hot needle punching, hot roll calendaring, ultrasonic perforation, or the like. Such mechanical processes may be cumbersome and/or difficult to control during high speed manufacture of composite materials. It is also to known to provide air and water vapor permeability to polymer films by including therein one or more pore-forming fillers such as calcium carbonate, followed by stretching of the films to form micropores in areas adjacent to the filler. However, it is often difficult to provide a desired degree of permeability in elastic films using such techniques. Accordingly, there is a continued desire for breathable elastic materials which may be easily manufactured.

SUMMARY OF THE INVENTION

It is therefore an object of the invention to provide improved breathable elastic composite materials and to provide improved methods for manufacturing such materials.

In one embodiment, the invention is directed to breathable, incrementally stretched elastic composite materials. The composite materials comprise an inner elastomeric film extrusion-laminated to an outer nonwoven web at each film surface. The inner elastomeric film has a random pattern of incremental stretch-formed macroholes therein and is substantially free of pore-forming filler.

In an alternate embodiment, the breathable, incrementally stretched elastic composite materials comprise an elastomeric film extrusion-laminated to a nonwoven web at one or both of the film surfaces. The elastomeric film has a random pattern of incremental stretch-formed macroholes therein and is substantially free of pore-forming filler.

In another embodiment, the invention is directed to garments. The garments are formed, at least in part, from a breathable, incrementally stretched elastic composite material according to the invention. In a further embodiment, the invention is directed to disposable articles formed, at least in part, from a breathable, incrementally stretched elastic composite material according to the invention.

In yet another embodiment, the invention is directed to methods of manufacturing a breathable elastomeric composite material. The methods comprise extrusion laminating an elastomeric film to at least one nonwoven web at a film surface to tightly bond the nonwoven web thereto, and incrementally stretching the resulting laminate to form a random pattern of macroholes in the elastomeric film. The elastomeric film is substantially free of pore-forming filler. In a specific embodiment, the elastomeric film is extrusion laminated to a nonwoven web at each film surface.

The composite materials according to the present invention are advantageous in exhibiting a desirable combination of breathability and elasticity and may be easily manufactured according to the inventive methods. These and additional objects and advantages will be more fully apparent in view of the following detailed description which illustrates various modes contemplated for carrying out the invention. As will be realized, the invention is capable of other different obvious aspects, all without departing from the invention. Accordingly, the drawings and specification are illustrative in nature and not restrictive.

BRIEF DESCRIPTION OF THE DRAWINGS

While the specification concludes with claims particularly pointing out and distinctly claiming the present invention, the invention will be further understood from the following detailed description taken in conjunction with the accompanying drawings in which:

DETAILED DESCRIPTION

The present invention is directed to breathable, incrementally stretched elastic composite materials. Within the context of the present specification, the term "breathable" means that the composite materials exhibit air permeability. In additional embodiments, the composite materials are both air and moisture vapor-permeable. In specific embodiments, the composite materials have an air permeability of at least about 10 cc/min/cm² when a pressure of about 60 psi is applied thereto. In a more specific embodiment, the composite materials may have an air permeability of at least about 15 cc/min/cm² when a pressure of about 60 psi is applied thereto. Within the context of the present specification, the term "elastic" means stretchable under force and recoverable to an original or essentially original form upon release of the stretching force, while the term "elastomeric" is used to describe an elastic polymer material. In specific embodiments, the composite materials have a stretchability of at least about 150% and, when the stretching force is released, a permanent set or elongation of not more than about 15%. In further embodiments, the composite material has a stretchability of at least about 200% and, when the stretching force is released, a permanent set or elongation of not more than about 25%. Finally, within the context of the present specification, the term "incrementally stretched" means that the composite material includes alternating stretched zones and non-stretched zones across its length. The incremental stretch process will be described in farther detail below.

Figure 1A:
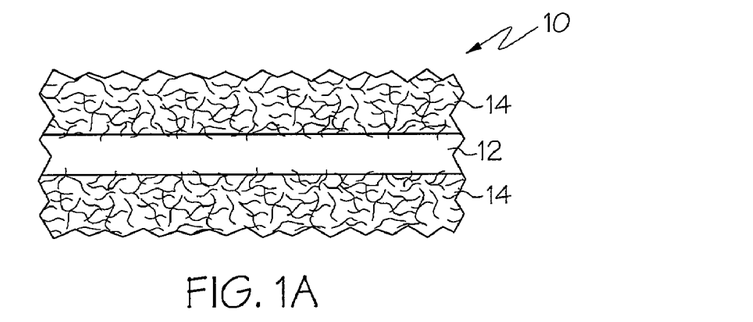
FIGS. 1A and 1B are schematic diagrams of cross-sectional views of first and second embodiments, respectively, of composite materials according to the present invention.
Figure 1B:
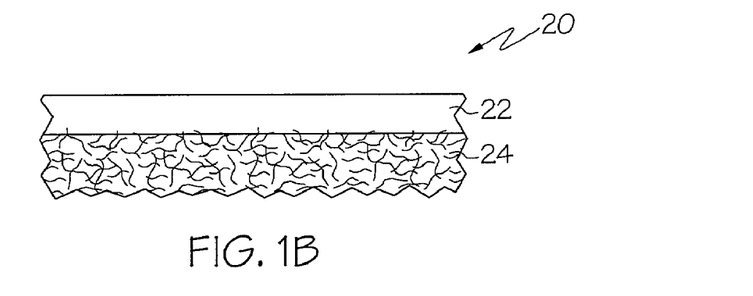

FIGS. 1A and 1B set forth cross-sectional schematic diagrams of first and second embodiments of composite materials according to the invention. In FIG. 1A, the composite material 10 comprises an inner elastomeric film 12 and an outer nonwoven web 14 at each film surface. The composite material 20 of FIG. 1B comprises an elastomeric film 22 having a nonwoven web 24 at one film surface. While many of the specific embodiments described herein will include two nonwoven webs along the lines of the composite material 10 of FIG. 1A, it should be understood that the invention as broadly disclosed encompasses composite material 20 as shown in FIG. 1B. Moreover, in the composite materials 10 and 20, the elastomeric films 12 and 22, respectively, are shown schematically as a single layer. It is equally within the scope of the invention that the elastomeric film comprises a multi-layer structure, as will be described in further detail below with respect to individual embodiments of the invention.

In the composite materials of the invention, the elastomeric film is extrusion laminated to a nonwoven web at one or both of the film surfaces. In accordance with an important feature of the invention, the extrusion lamination tightly bonds the elastomeric film to the nonwoven web or webs. Within the context of the present specification, the term "tightly bonded" means that the elastomeric film and the nonwoven web cannot be peeled apart from one another. Processing conditions suitable for providing a tight bond between the elastomeric film and the nonwoven web or webs will be discussed in further detail below. As a result of the tight bonding between these layers of the composite material, fibers from the nonwoven web are embedded into the film and, upon incremental stretching, a random pattern of macroholes or pinholes is produced in the elastomeric film to render the composite materials breathable. The random pattern is typically controlled and uniform in concentration along the length and width of the composite material. Additionally, the size of the macroholes is relatively uniform along the length and width of the composite material. In one embodiment, the composite materials are rendered breathable to such an extent that the materials are not liquid impervious. Thus, the composite materials according to such embodiments are suitable for applications wherein a liquid barrier is not required. Depending on the compositions and physical parameters of the elastomeric film and nonwoven webs, the degree of tight bonding therebetween and the incremental stretching process conditions, the size of the pinholes or macroholes formed in the elastomeric film may be controlled. In specific embodiments, the average diameter of the macroholes may range from about 5 μm to about 100 μm, more specifically from about 10 μm to about 50 μm, more specifically from about 15 μm to about 35 μm. These various conditions may also be used to control the concentration of pinholes or macroholes per surface area of composite material. While the concentration of macroholes may be varied depending on the particular use of the composite material, in specific embodiments, the concentration may range from about 5 to about 500 per inch$^2$, more specifically from about 10 to about 100 per inch$^2$, more specifically from about 25 to about 75 per inch$^2$.

The elastomeric film employed in the composite materials according to the present invention may comprise any elastomeric material which is capable of formation into a film by die extrusion. Additionally, the elastomeric film may comprise a single monolayer film or, alternatively, may comprise a multilayer film comprising two or more layers, which typically are coextruded. While the specific desired elasticity of a film and the resulting composite material will be determined based on the desired application of the composite material, in one embodiment, the elastomeric film exhibits a permanent set of less than about 20%, more specifically from about 12 to about 18%, at 200% elongation. In yet another embodiment, the elastomeric film exhibits a stress relaxation of about 15-20% at 200% elongation. Examples of suitable elastomeric materials include elastomeric block copolymers, elastomer metallocene polymers and copolymers, for example the elastomeric metallocene olefin copolymers, elastomeric polyurethane homopolymers and copolymers, elastomeric polysiloxane homopolymers and/or copolymers, and the like, and mixtures of such elastomeric materials. Nonelastic polymers may also be included therein as long as the resulting film exhibits the desired elastic properties.

Suitable elastomeric block copolymers include those having at least one vinyl aromatic block and at least one rubber block. Specific aromatic vinyl monomers for forming such block copolymers include styrene and substituted styrene monomers, for example alkyl-substituted styrenes and halogen-substituted styrenes, and mixtures thereof. The elastomeric block copolymers containing one or more of these styrene monomer blocks are commonly referred to as elastomeric styrenic block copolymers. Specific monomers for forming the rubber block include, but are not limited to, butadiene, isoprene, ethylene-propylene, ethylene-butylene, and the like. The block copolymers may comprise two blocks, three blocks or more. Commercially available block copolymers include the Kraton polymers available from Kraton Polymers, including, but not limited to, poly(styrene-butadiene-styrene), poly(styrene-isoprene-styrene), poly(styrene-ethylene-butylene-styrene), poly(styrene-ethylene-propylene-styrene), and the like.

The elastomeric metallocene olefin polymers and copolymers include, but are not limited to, polyolefins produced from the metallocene single-cite catalysts. Typically, one or more olefins such as ethylene, propylene, styrene or the like is polymerized with butene, hexene, octene, mixtures thereof or the like, to provide elastomers suitable for use in the present invention. Examples include, but are not limited to, poly(ethylene-butene), poly(ethylene-hexene), poly(ethylene-octene), poly(ethylene-propylene) and/or polyolefin terpolymers thereof.

Additional elastomeric materials for use in the elastomeric film layer of the invention include poly(ester-ether), poly(ether-amide), poly(ethylene-vinyl acetate), poly(ethylene-methylacrylate), poly(ethylene-acrylic acid), poly(ethylene butylacrylate), poly(ethylene-propylene-diene), and ethylene-propylene rubber.

In one embodiment, the elastomeric film comprises a blend of at least one elastomeric styrenic block copolymer and at least one elastomeric metallocene olefin copolymer. The respective amounts of the copolymers may be varied depending on the desired elastic properties of the composite material.

In a more specific embodiment, such blends comprise from about 10 to about 90 weight percent of the styrenic block copolymer and from about 10 to about 90 weight percent of the metallocene olefin copolymer. In a further embodiment, such blends comprise from about 50 to about 90 weight percent of the styrenic block copolymer and from about 10 to about 50 weight percent of the metallocene olefin copolymer.

In additional embodiments, the elastomeric film may comprise one or more core layers A and one or more cap or skin layers B. Generally, such cap or skin layers may be provided in order to chemically isolate one layer from another or to physically isolate a layer from an environment of use. For example, when a blend of a Kraton elastomeric styrenic block copolymer and a metallocene polyethylene is employed in the elastomeric film, the film tends to exhibit a sticky surface feel and it may be desirable to provide the elastomeric film surfaces with a cap layer on each surface. Typically, a thin layer of polyolefin, for example polyethylene, polypropylene, or mixtures thereof, may be used as such a cap layer on either side of the core blend layer, whereby the elastomeric film will comprise a multilayer film of the structure A/B/A. The cap layers may be conveniently provided by coextrusion with the core layer.

As the random pattern of incremental stretch-formed macroholes is formed in the elastomeric film by the incremental stretching process, it is not necessary to include any type of pore-forming filler in the elastomeric film. Thus, the elastomeric film is substantially free of pore-forming filler. Within the context of the present specification, the term "substantially free of pore-forming filler" means that the elastomeric film contains an insufficient amount of pore-forming filler to render the film microporous upon incremental stretching due to microvoid formation adjacent the filler. In more specific embodiments, the elastomeric film contains less than about 20 weight percent pore-forming filler, more specifically, less than about 10 weight percent pore-forming filler, and yet more specifically, less than about 5 weight percent pore-forming filler. In further embodiments, the elastomeric film contains less than about 1 weight percent of the pore-forming filler. In a further embodiment, the elastomeric film does not contain any pore-forming filler.

The weight or thickness of the elastomeric film may be adjusted depending on the properties desired for the composite material. Typically, the elastomeric film may have a gauge of from about 25 to about 70 grams/m$^2$, and in more specific embodiments, the elastomeric film may have a gauge of from about 30 to about 40 grams/m$^2$.

As used herein "nonwoven fibrous web" is used in its generic sense to define a generally planar structure that is relatively flat, flexible and porous, and is composed of staple fibers or continuous filaments. For a detailed description of nonwovens, see "Nonwoven Fabric Primer and Reference Sampler" by E. A. Vaughn, Association of the Nonwoven Fabrics Industry, 3d Edition (1992). The nonwovens may be prepared by any conventional process, and may be, among others, carded, spun bonded, wet laid, air laid or melt blown, or any combination thereof, as such products are well known in the trade. The nonwoven fibrous webs may comprise fibers of polyolefins, including, but not limited to, polyethylene and/or polypropylene, and including metallocene-catalyzed polyolefins, polyesters, rayon, cellulose, nylon, and blends of such fibers. The fibers may also comprise bicomponent fibers, formed from two or more materials in any physical arrangement.

In one embodiment, the nonwoven web is not itself elastic. In a more specific embodiment, the nonwoven is stretchable, i.e., it elongates under force, even if it is not recoverable to its original form upon release of the stretching force. Typically, nonwovens which are loosely formed may be more highly stretchable. In further embodiments, the nonwoven may be elastic. In one embodiment, the nonwoven web has a weight of less than about 40 g/m$^2$. In a more specific embodiment, the nonwoven web has a weight of less than about 25 g/m$^2$. In yet a further embodiment, the nonwoven web has a weight of about 12 g/m$^2$.

In specific embodiments, the nonwoven web may comprise a spun-bonded polyolefin, for example spun-bonded polyethylene or spun-bonded polypropylene. Various spun-bonded polyolefin webs are commercially available and are suitable for use in the invention. Spun-bonded webs formed from polyethylene and polypropylene are also suitable. For example, spun-bonded nonwovens formed from fibers which comprise a blend of polyethylene and polypropylene, at any proportion, and/or formed from fibers which comprise a coextrusion of polyethylene and polypropylene, are also suitable. These nonwovens are commercially available, for example, from BBA.

The composite materials according to the present invention may be used in various applications where breathability, for example air and moisture vapor permeability, and elastomeric properties are desired. In one embodiment, the composite materials are employed in the formation of garments, including diapers, pants, surgical gowns and the like. The composite materials are also advantageous for use in forming disposable articles, including disposable garments of the type described above. Additionally, the composite materials may be employed in the formation of disposable sheets, dressings, hygienic products and the like. In a preferred embodiment, the composite materials of the invention are employed in baby diapers and baby training pants in areas where liquid impermeability is not required, i.e., in side areas commonly referred to as "diaper ears." The composite materials exhibit a good combination of elasticity and retaining force, together with good breathability and softness, for advantageous use in such applications.

In accordance with an important feature, the composite materials of the invention may be easily manufactured. Specifically, the elastomeric film is extrusion laminated to an outer nonwoven web at at least one film surface, to tightly bond the nonwoven web thereto. In a more specific embodiment, the elastomeric film is extrusion laminated to an outer nonwoven web at each film surface to tightly bond the nonwoven webs thereto. The extrusion lamination of the elastomeric film and the one or more nonwoven webs may be conducted according to any conventional extrusion lamination techniques. Importantly, the extrusion lamination is conducted under conditions which tightly bond the elastomeric film with the nonwoven webs. The resulting laminate is then incrementally stretched to form a random pattern of macroholes in the inner elastomeric film. As discussed above, the elastomeric film is substantially free of pore-forming filler.

The incremental stretching is preferably conducted in a cross direction, referred to herein as CD intermesh stretching. A CD intermeshing stretcher typically comprises a pair of gear-like elements on parallel shafts. The shafts are disposed between two machine side plates, the lower shaft being located in fixed bearings and the upper shaft being located in bearings in vertically slidable members. The slidable members are adjustable in the vertical direction by wedge shaped elements operable by adjusting screws. Screwing the wedges out or in will move the vertically slidable member respectively down or up to further engage or disengage the gear-like teeth of the upper intermeshing roll with the lower intermeshing roll. Micrometers mounted to the side frames are operable to indicate the depth of engagement of the teeth of the intermeshing roll. Air cylinders are typically employed to hold the slidable members in their lower engaged position firmly against the adjusting wedges to oppose the upward force exerted by the material being stretched. These cylinders may also be retracted to disengage the upper and lower intermeshing rolls from each other for purposes of threading material through the intermeshing equipment or in conjunction with a safety circuit which would open all the machine nip points when activated. The drive for the CD intermeshing stretcher must operate both upper and lower intermeshing rolls except in the case of intermeshing stretching of materials with a relatively high coefficient of friction.

The CD intermeshing elements are typically machined from solid material but can best be described as an alternating stack of two different diameter disks. In one embodiment, the intermeshing disks are about 6" in diameter, about 0.031" thick, and have a full radius on their edge. The spacer disks separating the intermeshing disks are about 5.5" in diameter and about 0.069" in thickness. Two rolls of this configuration would be able to be intermeshed up to 0.231" leaving 0.019" clearance for material on all sides. This CD intermeshing element configuration would have a 0.100" pitch.

The engagement of the CD intermeshing roll elements may be adjusted in order to provide the macroholes in the elastomeric film. In one embodiment, the engagement of the intermeshing roll elements is at least about 0.12 inch, more specifically from about 0.12 inch to about 0.20 inch.

Since the CD intermeshing elements are typically capable of large engagement depths, it is important that the equipment incorporate a means of causing the shafts of the two intermeshing rolls to remain parallel when the top shaft is raising or lowering. This is necessary to assure that the teeth of one intermeshing roll always fall between the teeth of the other intermeshing roll and potentially damaging physical contact between intermeshing teeth is avoided. This parallel motion may be assured by a rack and gear arrangement wherein a stationary gear rack is attached to each side frame in juxtaposition to the vertically slidable members. A shaft traverses the side frames and operates in a bearing in each of the vertically slidable members. A gear resides on each end of this shaft and operates in engagement with the racks to produce the desired parallel motion.

If desired, the composite material may also be subjected to machine direction (MD) intermeshing stretching, although MD stretching may typically not be necessary as sufficient breathability is provided by the CD intermesh stretching. The MD intermeshing stretching equipment is typically identical to the CD intermeshing stretching equipment except for the design of the intermeshing rolls. The MD intermeshing rolls closely resemble fine pitch spur gears. In one embodiment, the rolls have a 5.933" diameter, 0.100" pitch, 30 diametral pitch, 141/2. degree. pressure angle, and are basically a long addendum, topped gear. A second pass may be taken on these rolls with the gear hob offset 0.010" to provide a narrowed tooth with more clearance. With about 0.090" of engagement, this configuration will have about 0.010" clearance on the sides for material thickness. If desired, additional stretching may be performed, including tenter or machine direction orientation stretching, although, as noted above, for many applications, the CD intermeshing stretching will be sufficient.

Figure 2:
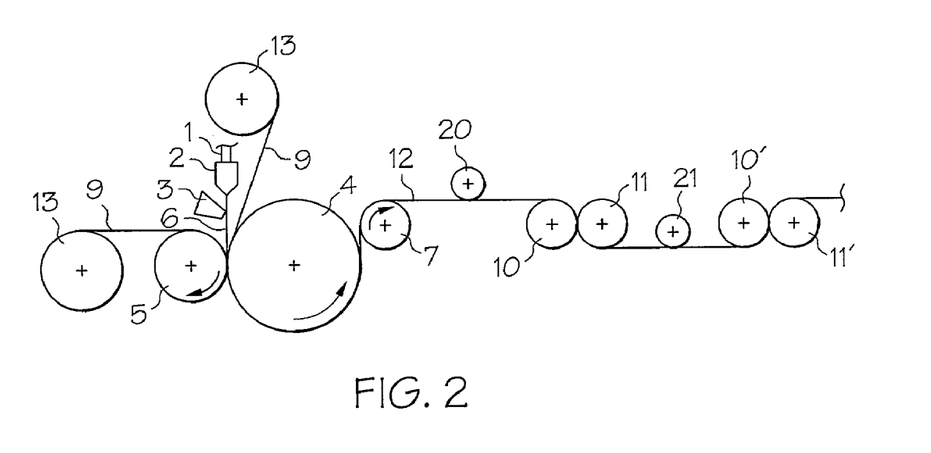
FIG. 2 is a schematic diagram of an extrusion lamination section and an incremental stretch section of an apparatus suitable for use in an embodiment of the methods according to the invention.

FIG. 2 sets forth a schematic representation of one embodiment of the methods of the invention. An elastomeric film 6 is extruded from an extruder 1 through a die 2 and past an air knife 3, into a nip formed between rolls 4 and 5. The extrusion is conducted at or above the melt temperature of the film material, typically on the order of about 400-500° F. Conventionally, roll 4 may be a metal roll while roll 5 may be a rubber roll. Two nonwoven webs 9, 9 are supplied from rolls 13, 13 and the film 6 and webs 9 are passed through the nip of rolls 4 and 5 to laminate the webs to the film surfaces. The nip pressure is adjusted in order to obtain the desired tight bond between the nonwoven webs and the elastomeric film. Typically, pressures of greater than about 50 pounds per linear inch are employed. In a more specific embodiment, the nip pressure is from about 50 to about 150 pounds per linear inch, more specifically from about 50 to about 120 pounds per linear inch. The resulting laminate 12 is conducted by roll 7 past an optional preheated roller 20 and to the incremental stretch section where the laminate is passed through incremental cross direction (CD) stretcher rollers 10 and 11 to form the breathable, incrementally stretched elastomeric composite material 14. The material 14 may optionally be passed through an additional stretch section where it is subjected to further stretching. For example, the material 14 is shown in FIG. 2 as passing a further preheated roller 21 and through incremental machine direction (MD) stretcher rollers 10' and 11'. One skilled in the art will appreciate that preheated rollers 20 and 21 may be omitted if desired.

The following examples demonstrate specific embodiments of the multilayer microporous films according to the invention, In the examples, and throughout the specification, parts and percentages are by weight unless otherwise specified.

EXAMPLE 1

In this example, a composite material according to the invention is prepared. A blend comprising about 70 weight percent poly(styrene-butadiene-styrene) block copolymer elastomer and about 30 weight percent of a metallocene polyethylene plastomer is extruded using conventional film extrusion techniques. The blend is coextruded as a core layer B with outer layers A comprising a mixture of about 80 weight percent very low density polyethylene (VLDPE) and about 20 weight percent low density polyethylene (LDPE) to form an elastomeric film of the structure A/B/A.

The resulting elastomeric film is extrusion laminated on each film surface with a high stretchable spun bonded polyethylene nonwoven web having a weight of about 30 grams/m$^2$. A nip pressure of about 60 pounds per linear inch is used to form a tight bond between the nonwoven webs and the elastomeric film. The laminate is then incrementally stretched using CD intermeshing stretching, with a roll engagement depth of about 0.120 inch.

The resulting composite material has a weight of about 95 grams/m$^2$ and exhibits good breathability, good elasticity and a soft feel. When stretched about 100%, the composite material exhibits about 7% permanent set.

Figure 3:
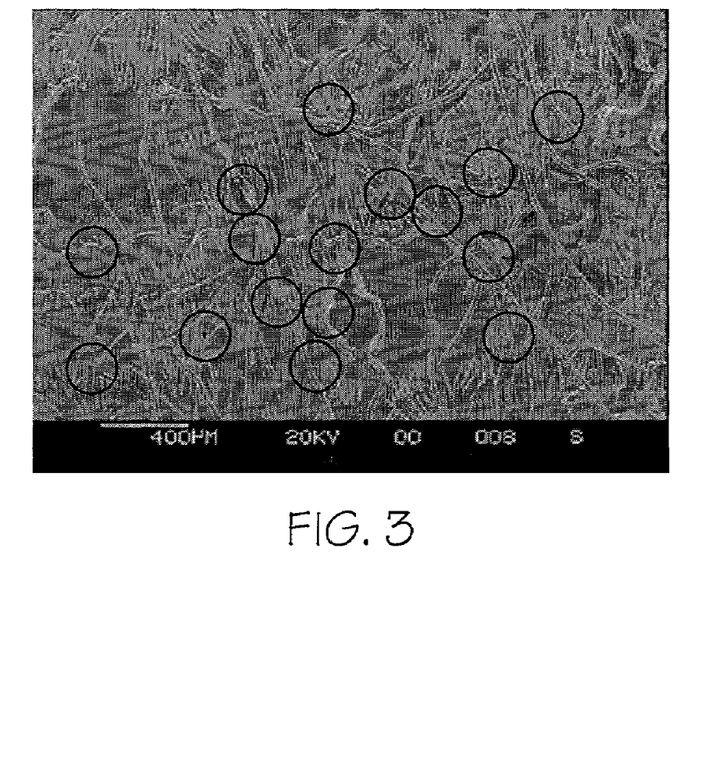
FIG. 3 is an enlarged (50×) view of an inner elastomeric film layer of a composite material according to the present invention as described in Example 1.
Figure 4:
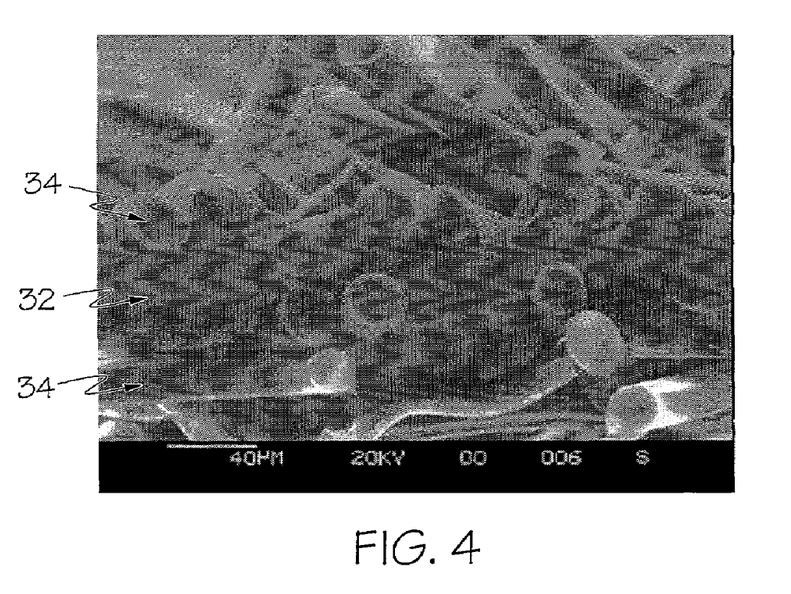
FIG. 4 is an enlarged (500×) cross-sectional view of a composite material according to the invention as described in Example 1.
Figure 5:
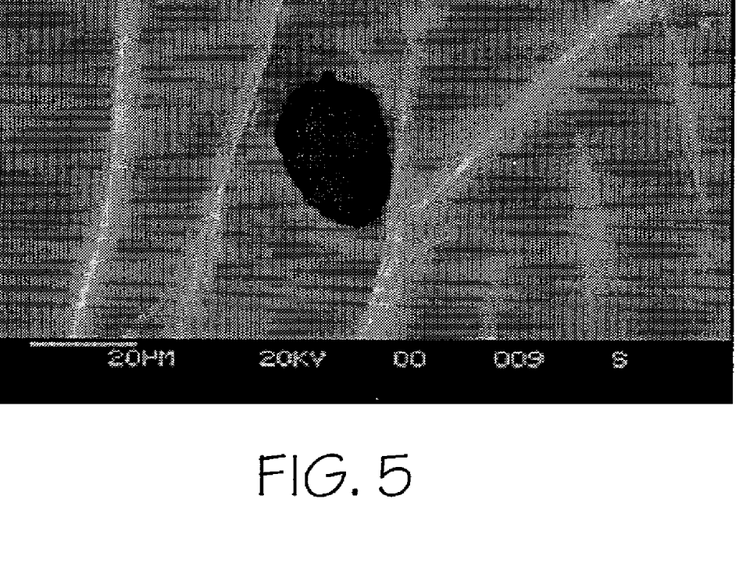
FIG. 5 is an enlarged (1000×) view of an inner elastomeric film layer of a composite material according to the present invention as described in Example 1.

FIGS. 3-5 show enlarged views of the composite material. Specifically, FIG. 3 comprises a 50× enlargement of the stretched elastomeric film of the composite material, with macroholes therein appearing in the circled areas. FIG. 4 comprises a 500× enlargement of the composite material, with the elastomeric film layer indicated at 32 and the nonwoven web layers indicated at 34. This view shows the tight bonding between the film and the nonwoven webs. FIG. 5 comprises a 1000× enlargement of the stretched elastomeric film of the composite material, with one macrohole shown therein having a diameter of about 20 μm.

Figure 6:
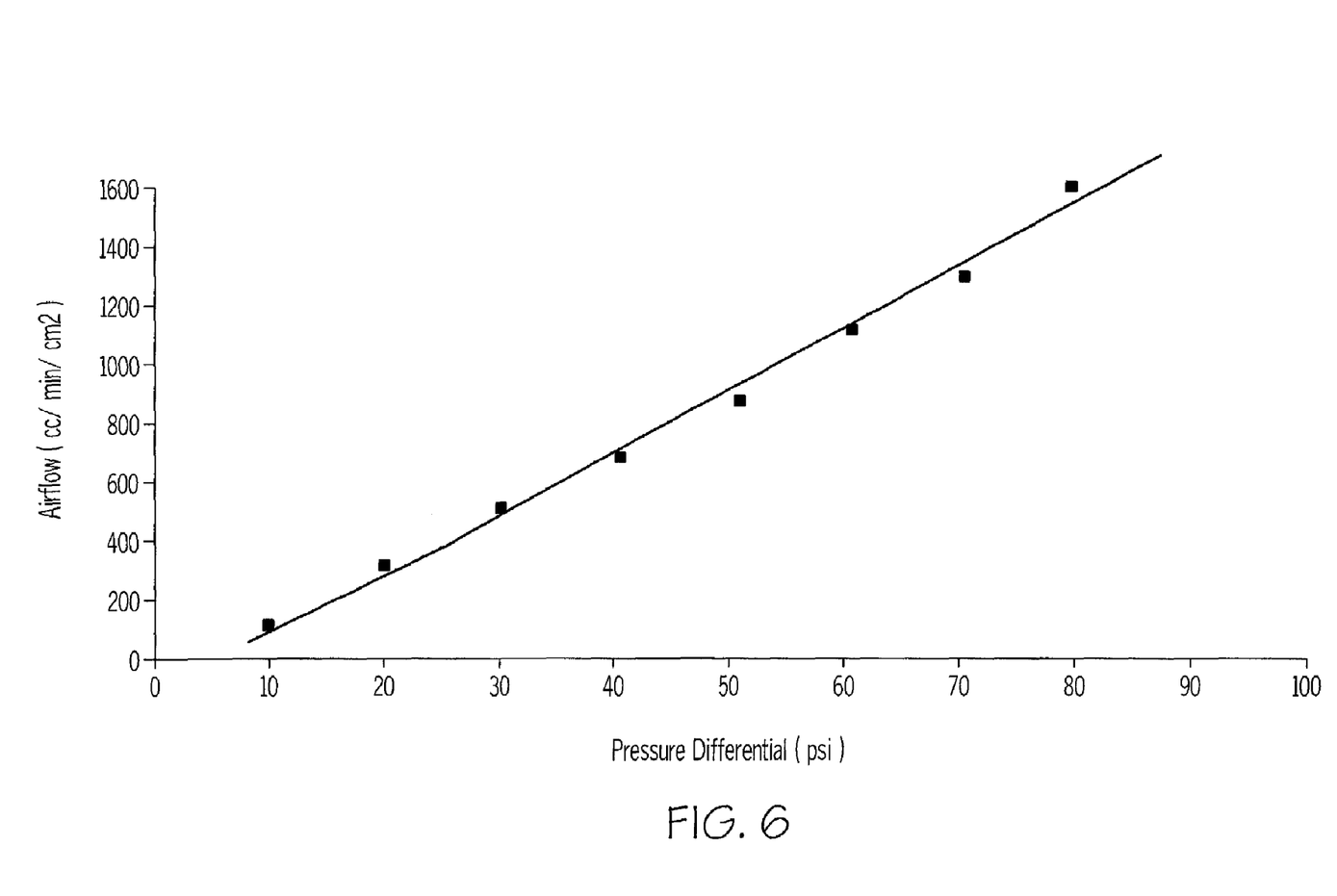
FIG. 6 graphically sets forth the air permeability of a composite film according to the invention as described in Example 1, as a function of pressure differential.

The composite material of this example is subjected to measurement of airflow therethrough as a function of applied air pressure. The results are shown in FIG. 6 wherein air flow is indicated in cc/min/cm$^2$ and pressure is indicated in pounds per square inch.

Interestingly, it has been determined that composite materials according to the present invention are not only stretchable and recoverable, but also exhibit increased air permeability in their stretched state. In this example, the air permeability of the composite material is measured, in cubic feet per minute, as a function of the percent stretching. A "TexTest Air Permeability Tester," Model FX 3300, available from ATI (Advanced Testing Instruments) Corporation of Spartansburg, S.C., at a pressure of 125 Pa (0.018 psi) is employed. The results are set forth in Table 1.

TABLE 1

| Measurement | Percent Stretched | CFM |
|---|---|---|
| 1 | 0 | 0.16 |
| 2 | 50 | 0.44 |
| 3 | 100 | 0.85 |
| 4 | 150 | 1.10 |

The results in Table 1 demonstrate the increased air permeability of the composite material of this example upon stretching.

EXAMPLE 2

In this example, a composite material according to the invention is prepared. An elastomeric film is prepared by extrusion laminating a blend of 90 weight percent poly(styrene-butadiene-styrene) block copolymer elastomer and about 10 weight percent of ethylene vinyl acetate copolymer. The elastomeric film is extrusion laminated on each film surface with a stretchable spun-bonded polypropylene nonwoven web. A nip pressure of about 60 pounds per linear inch is used to form a tight bond between the nonwoven webs and the elastomeric film. The laminate is preheated using a preheated roller having a temperature of about 210° F. and is incrementally stretched using CD intermeshing stretching, with a roll engagement depth of about 0.130 inch.

The resulting composite material is stretchable and recoverable, exhibits good breathability, good elasticity and a soft feel. When stretched to about 200%, the composite material exhibits about 20% permanent set. The composite material has a weight of about 88 g/m$^2$.

The air permeability of the composite material of this example is measured in accordance with the procedures and apparatus described in Example 1. The results are set forth in Table 2.

TABLE 2

| Measurement | Percent Stretched | CFM |
|---|---|---|
| 1 | 0 | 0.08 |
| 2 | 50 | 0.78 |
| 3 | 100 | 1.09 |
| 4 | 150 | 1.15 |

Thus, the composite material of this example exhibits increased air permeability upon stretching.

The specific illustrations and embodiments described herein are exemplary only in nature and are not intended to be limiting of the invention defined by the claims. Further embodiments and examples will be apparent to one of ordinary skill in the art in view of this specification and are within the scope of the claimed invention.

What is claimed is:

1. A breathable, incrementally stretched elastic composite material comprising an inner elastomeric film extrusion-laminated to an outer nonwoven web at each film surface, wherein the inner elastomeric film has a random pattern of incremental stretch-formed macroholes having an average diameter of from about 10 μm to about 100 μm therein, and wherein the inner elastic film contains an insufficient amount of pore-forming filler to render the film microporous upon incremental stretching due to microvoid formation adjacent the filler, wherein the concentration of macroholes therein is in a range of from about 5 to about 500 per inch$^2$.

2. The composite material of claim 1, having an air permeability of at least about 10 cc/min/cm$^2$ when a pressure of about 60 psi is applied thereto.

3. The composite material of claim 1, having a stretchability of at least about 200% with a permanent set of no more than about 25%.

4. The composite material of claim 1, wherein the inner elastomeric film comprises elastomeric block copolymer, elastomeric metallocene olefin polymer or copolymer, elastomeric polyurethane, elastomeric polysiloxane, or mixtures thereof.

5. The composite material of claim 4, wherein the inner elastomeric film comprises an elastomeric styrenic block copolymer.

6. The composite material of claim 5, wherein the inner elastomeric film comprises poly(styrene-butadiene-styrene), poly(styrene-isoprene-styrene), poly(styrene-ethylene-butylene-styrene), or combinations thereof.

7. The composite material of claim 5, wherein the inner elastomeric film comprises a blend of an elastomeric styrenic block copolymer and an elastomeric metallocene polyethylene copolymer.

8. The composite material of claim 1, wherein the inner elastomeric film is a monolayer film.

9. The composite material of claim 1, wherein the inner elastomeric film comprises a multilayer film.

10. The composite material of claim 9, wherein the inner elastomeric film comprises a core layer including an elastomeric styrene block copolymer, coextruded at each surface with a polyolefin cap layer.

11. The composite material of claim 1, wherein the nonwoven webs individually comprise spun bonded polyolefin.

12. The composite material of claim 1, wherein each nonwoven web has a weight of less than about 40 g/m$^2$.

13. The composite material of claim 1, wherein, each nonwoven web has a weight of about 12 g/m$^2$.

14. A garment formed at least in part from the composite material of claim 1.

15. A disposable article formed at least in part from the composite material of claim 1.

16. The disposable article of claim 15, comprising a diaper.

17. A breathable, incrementally stretched elastic composite material comprising an inner elastomeric film including a blend of an elastomeric styrenic block copolymer and an elastomeric metallocene polyethylene copolymer extrusion-laminated to an outer nonwoven spun bonded polyolefin web at each film surface, wherein the inner elastomeric film has a random pattern of incremental-stretch formed macroholes having an average diameter of from about 10 μm to about 100 μm therein, and wherein the inner elastic film contains an insufficient amount of pore-forming filler to render the film microporous upon incremental stretching due to microvoid formation adjacent the filler, wherein the concentration of macroholes therein is in a range of from about 5 to about 500 per inch$^2$.

18. A garment formed at least in part from the composite material of claim 17.

19. A disposable article formed at least in part from the composite material of claim 17.

20. The disposable article of claim 19, comprising a diaper.

21. A breathable, incrementally stretched elastic composite material, comprising an elastomeric film extrusion-laminated to a nonwoven web at one or both of the film surfaces, wherein the elastomeric film has a random pattern of incremental stretch-formed macroholes having an average diameter of from about 10 μm to about 100 μm therein, and wherein the elastic film contains an insufficient amount of pore-forming filler to render the film microporous upon incremental stretching due to microvoid formation adjacent the filler, wherein the concentration of macroholes therein is in a range of from about 5 to about 500 per inch$^2$.

22. A garment formed at least in part from the composite material of claim 21.

23. A disposable article formed at least in part from the composite material of claim 21.

24. The disposable article of claim 23, comprising a diaper.

25. A method of manufacturing a breathable elastomeric composite material as defined in claim 1, comprising
extrusion laminating the inner elastomeric film to the outer nonwoven web at each film surface to tightly bond the nonwoven webs thereto; and
incrementally stretching the resulting laminate to form the random pattern of macroholes in the inner elastomeric film.

26. The method of claim 25, wherein the extrusion lamination is conducted at a nip pressure of greater than about 50 pounds per linear inch.

27. The method of claim 25, wherein the incremental stretching comprises cross direction (CD) intermesh stretching.

28. The method of claim 27, wherein the CD intermesh stretching employs an intermeshing roll engagement of at least about 0.12 inch.

29. The method of claim 25, wherein the composite material has an air permeability of at least about 10 cc/min/cm$^2$ when a pressure of about 60 psi is applied thereto.

30. The method of claim 25, wherein the composite material has a stretchability of at least about 200% with a permanent set of no more than about 25%.

31. The method of claim 25, wherein the inner elastomeric film comprises an elastomeric styrenic block copolymer.

32. The method of claim 25, wherein the inner elastomeric film comprises a blend of an elastomeric styrenic block copolymer and an elastomeric metallocene polyethylene copolymer.

33. The method of claim 25, wherein the inner elastomeric film comprises a core layer including an elastomeric styrene block copolymer, coextruded at each surface with a polyolefin cap layer.

34. The method of claim 25, wherein the nonwoven webs individually comprise spun bonded polyolefin.

35. The method of claim 25, wherein each nonwoven web has a weight of less than about 40 g/m$^2$.

36. The method of claim 25, wherein, each nonwoven web has a weight of about 12 g/m$^2$.

37. A method of manufacturing a breathable elastomeric composite material as defined in claim 21, comprising
extrusion laminating the elastomeric film to the outer nonwoven web at one or both of the film surfaces to tightly bond the nonwoven web thereto; and
incrementally stretching the resulting laminate to form the random pattern of macroholes in the elastomeric film.

38. The composite material of claim 1, wherein the macroholes have an average diameter of from about 10 μm to about 50 μm.

39. The composite material of claim 1, wherein the macroholes have an average diameter of from about 15 μm to about 35 μm.

40. The composite material of claim 1, wherein the concentration of macroholes therein is in a range of from about 10 to about 100 per inch$^2$.

41. The composite material of claim 1, wherein the concentration of macroholes therein is in a range of from about 25 to about 75 per inch$^2$.

42. The composite material of claim 17, wherein the macroholes have an average diameter of from about 10 μm to about 50 μm.

43. The composite material of claim 17, wherein the macroholes have an average diameter of from about 15 μm to about 35 μm.

44. The composite material of claim 17, wherein the concentration of macroholes therein is in a range of from about 10 to about 100 per inch$^2$.

45. The composite material of claim 17, wherein the concentration of macroholes therein is in a range of from about 25 to about 75 per inch$^2$.

46. The composite material of claim 21, wherein the macroholes have an average diameter of from about 10 μm to about 50 μm.

47. The composite material of claim 21, wherein the macroholes have an average diameter of from about 15 μm to about 35 μm.

48. The composite material of claim 21, wherein the concentration of macroholes therein is in a range of from about 10 to about 100 per inch$^2$.

49. The composite material of claim 21, wherein the concentration of macroholes therein is in a range of from about 25 to about 75 per inch$^2$.

50. The composite material of claim 1, wherein the inner elastomeric film contains less than about 10 weight percent pore-forming filler.

51. The composite material of claim 1, wherein the inner elastomeric film contains less than about 5 weight percent pore-forming filler.

52. The composite material of claim 1, wherein the inner elastomeric film contains less than about 1 weight percent pore-forming filler.

53. The composite material of claim 17, wherein the inner elastomeric film contains less than about 10 weight percent pore-forming filler.

54. The composite material of claim 17, wherein the inner elastomeric film contains less than about 5 weight percent pore-forming filler.

55. The composite material of claim 17, wherein the inner elastomeric film contains less than about 1 weight percent pore-forming filler.

56. The composite material of claim 21, wherein the elastomeric film contains less than about 10 weight percent pore-forming filler.

57. The composite material of claim 21, wherein the elastomeric film contains less than about 5 weight percent pore-forming filler.

58. The composite material of claim 21, wherein the elastomeric film contains less than about 1 weight percent pore-forming filler.

59. A breathable, incrementally stretched elastic composite material comprising an inner elastomeric film extrusion-laminated to an outer nonwoven web at each film surface, wherein the inner elastomeric film has a random pattern of incremental stretch-formed macroholes having an average diameter of from about 10 μm to about 100 μm therein and contains less than about 20 weight percent pore-forming filler, wherein the concentration of macroholes therein is in a range of from about 5 to about 500 per inch$^2$.

60. A breathable, incrementally stretched elastic composite material comprising an inner elastomeric film including a blend of an elastomeric styrenic block copolymer and an elastomeric metallocene polyethylene copolymer extrusion-laminated to an outer nonwoven spun bonded polyolefin web at each film surface, wherein the inner elastomeric film has a random pattern of incremental-stretch formed macroholes having an average diameter of from about 10 μm to about 100 μm therein and contains less than about 20 weight percent pore-forming filler, wherein the concentration of macroholes therein is in a range of from about 5 to about 500 per inch$^2$.

61. A breathable, incrementally stretched elastic composite material, comprising an elastomeric film extrusion-laminated to a nonwoven web at one or both of the film surfaces, wherein the elastomeric film has a random pattern of incremental stretch-formed macroholes having an average diameter of from about 10 μm to about 100 μm therein and contains less than about 20 weight percent pore-forming filler, wherein the concentration of macroholes therein is in a range of from about 5 to about 500 per inch$^2$.

\* \* \* \* \*